(12) United States Patent
Yamazaki (10) Patent No.: US 8,858,427 B2
(45) Date of Patent: Oct. 14, 2014

(54) ENDOSCOPE

(75) Inventor: Toshikazu Yamazaki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 17 days.

(21) Appl. No.: 13/314,422

(22) Filed: Dec. 8, 2011

(65) Prior Publication Data

US 2012/0165605 A1    Jun. 28, 2012

Related U.S. Application Data

(63) Continuation of application No. PCT/JP2011/066264, filed on Jul. 15, 2011.

(30) Foreign Application Priority Data

Aug. 5, 2010 (JP) ................................. 2010-176517

(51) Int. Cl.
| | | |
|---|---|---|
| *A61B 1/04* | (2006.01) | |
| *A61B 1/005* | (2006.01) | |
| *G02B 23/24* | (2006.01) | |
| *A61B 1/05* | (2006.01) | |
| *A61B 1/00* | (2006.01) | |

(52) U.S. Cl.
CPC ........... *A61B 1/0052* (2013.01); *A61B 1/00066* (2013.01); *G02B 23/2476* (2013.01); *A61B 1/05* (2013.01)
USPC .......................................... 600/131; 600/104

(58) Field of Classification Search
CPC ........... A61B 1/00052; A61B 1/00066; A61B 1/00068
USPC ......... 600/102, 118, 122, 131, 132, 146, 147, 600/149, 104; D24/138
See application file for complete search history.

(56) References Cited

U.S. PATENT DOCUMENTS

| 4,566,437 A | * | 1/1986 | Yamaguchi | ................... 600/131 |
| 5,785,644 A | * | 7/1998 | Grabover et al. | ............. 600/131 |

(Continued)

FOREIGN PATENT DOCUMENTS

| JP | 59-139235 A | 8/1984 |
| JP | 60-171402 | 11/1985 |

(Continued)

OTHER PUBLICATIONS

Extended Supplementary European Search Report dated Oct. 22, 2012 received in corresponding Application No. / Patent No. 11814440.1-1265 / 2502548 PCT/JP2011066264.

(Continued)

*Primary Examiner* — Alireza Nia
*Assistant Examiner* — Timothy J Neal
(74) *Attorney, Agent, or Firm* — Scully, Scott, Murphy & Presser, PC (57) ABSTRACT

An endoscope includes: an insertion portion configured to be inserted into a subject; an image pickup section configured to pick up an image of inside of the subject; an operation portion configured to be connected to the insertion portion; a grasping portion configured to be able to be grasped by an operator, the grasping portion being connected to the operation portion and provided such that an axis in a longitudinal direction is substantially perpendicular to a central axis of the insertion portion; a protruding portion provided on a surface on the insertion portion side of the grasping portion, the protruding portion protruding so as to form an acute angle with respect to the central axis of the insertion portion, on the insertion portion side; and a switch portion provided on the protruding portion and disposed at an angle which makes a right angle with respect to the acute angle.

7 Claims, 7 Drawing Sheets

(56) References Cited

U.S. PATENT DOCUMENTS

| | | | |
|---|---|---|---|
| D560,804 S * | 1/2008 | Pease et al. | D24/138 |
| 2003/0092965 A1 | 5/2003 | Konomura et al. | |
| 2008/0262307 A1 * | 10/2008 | Kakuto et al. | 600/118 |

FOREIGN PATENT DOCUMENTS

| | | |
|---|---|---|
| JP | 62-8727 | 1/1987 |
| JP | S63-68301 U | 5/1988 |
| JP | H02-141404 U | 11/1990 |
| JP | 3-97429 | 4/1991 |
| JP | 2000-342535 A | 12/2000 |
| JP | 2000-112945 A | 4/2002 |
| JP | 2002-112945 A | 4/2002 |
| JP | 2004-081797 A | 3/2004 |
| JP | 2004-109222 A | 4/2004 |
| JP | 2005-279120 A | 10/2005 |
| JP | 2006-142039 A | 6/2006 |
| JP | 2006-175248 A | 7/2006 |
| JP | 2008-302242 A | 12/2008 |
| JP | 2009-189684 A | 8/2009 |
| JP | 2010-207598 A | 9/2010 |

OTHER PUBLICATIONS

Japanese Office Action dated Feb. 7, 2012 in corresponding Japanese Patent Application No. 2011-551136.

* cited by examiner

ENDOSCOPE

CROSS REFERENCE TO RELATED APPLICATION

This application is a continuation application of PCT/JP2011/066264 filed on Jul. 15, 2011 and claims benefit of Japanese Application No. 2010-176517 filed in Japan on Aug. 5, 2010, the entire contents of which are incorporated herein by this reference.

BACKGROUND OF THE INVENTION

1. Field of the Invention

The present invention relates to an endoscope including a bending operation lever which rotates around an axis perpendicular to a central axis direction of an insertion portion.

2. Description of the Related Art

Endoscopes capable of performing observation and the like by inserting an elongated insertion portion into a subject have been widely used. Endoscopes include a type in which a bending portion is provided on a distal end side of an elongated insertion portion.

Japanese Patent Application Laid-Open Publication No. 2002-112945, for example, discloses an operation portion of an endoscope, which is held in a hand of an operator without slipping even if the operator loosens a grip and which makes the operator feel less fatigue on his/her hand even if an endoscopic examination continues for a long time. The endoscope is provided with a bending operation knob on one surface side of a wide surface of the operation portion including a grasping portion. When inserting the insertion portion of the endoscope into a body of a patient through the oral cavity or the anus of the patient lying on a bed, for example, an operator grasps the grasping portion with his/her left hand and grasps the insertion portion with his/her right hand, for example. Then, the operator operates the bending operation knob with his/her left hand grasping the grasping portion, thereby causing the bending portion to perform bending action, to change the orientation of the distal end portion of the insertion portion.

Japanese Patent Application Laid-Open Publication No. 2009-189684 discloses a gun-type endoscope in which an operation grasping portion is bent. In the endoscope, an operation lever for bending a bending portion is configured to rotate while facing the rear surface of the operation portion. According to the endoscope, an operator can grasp the operation grasping portion in a stable state without twisting his/her wrist, thereby capable of obtaining stable insertion performance. In addition, the operator can grasp the operation grasping portion with his/her right hand or left hand, and can operate the operation lever with the thumb of the hand grasping the operation lever.

SUMMARY OF THE INVENTION

An endoscope according to one aspect of the present invention includes: an insertion portion configured to be inserted into a subject; an image pickup section configured to pick up an image of inside of the subject; an operation portion configured to be connected to the insertion portion; a grasping portion configured to be able to be grasped by an operator, the grasping portion being connected to the operation portion and provided such that an axis in a longitudinal direction is substantially perpendicular to a central axis of the insertion portion; a protruding portion provided on a surface on the insertion portion side of the grasping portion, the protruding portion protruding so as to form an acute angle with respect to the central axis of the insertion portion, on the insertion portion side; and a switch portion provided on the protruding portion and disposed at an angle which makes a right angle with respect to the acute angle.

DETAILED DESCRIPTION OF THE PREFERRED EMBODIMENT(S)

Hereinafter, embodiments of the present invention will be described with reference to drawings.

Figure 1:
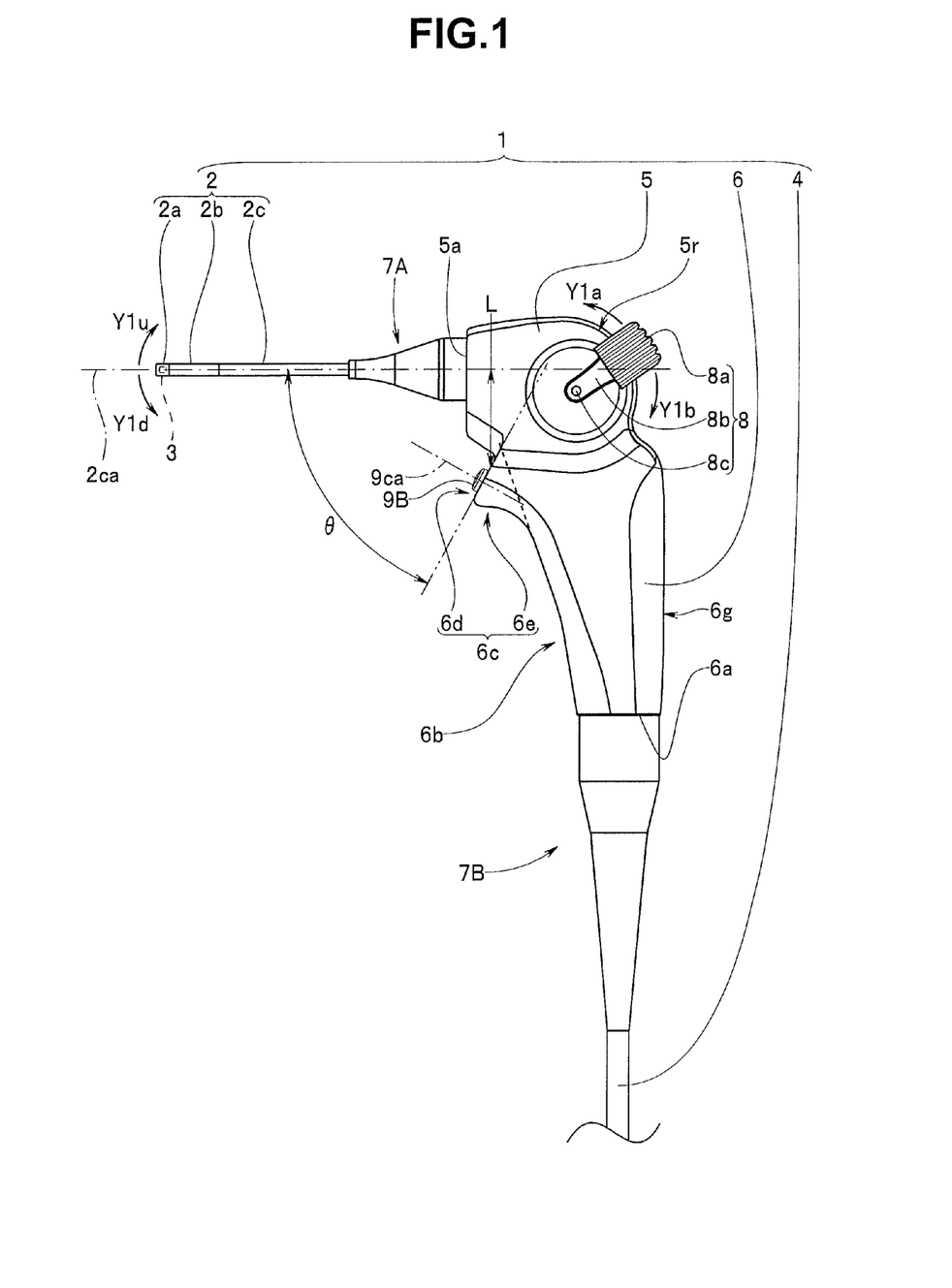
FIG. 1 is a view illustrating a configuration of an endoscope.

As shown in FIG. 1, an endoscope 1 is configured by mainly including an insertion portion 2, an operation portion 5, a grasping portion 6, and a universal cable 4.

The insertion portion 2 is inserted into a nasal cavity, for example. The insertion portion 2 is configured by including in the following order from a distal end side: a distal end portion 2a; a bending portion 2b; and a flexible tube portion 2c, which are provided in a linked manner.

The distal end portion 2a incorporates inside thereof an image pickup section 3 provided with an image pickup device such as a CCD, C-MOS, and the like which picks up an image of a portion to be examined.

The bending portion 2b bends in up and down directions, for example. The bending portion 2b bends in the up direction to cause the distal end portion 2a to move in the up direction as shown by the arrow Y1u in the drawing. On the other hand, the bending portion 2b bends in the down direction to cause the distal end portion to move in the down direction as shown by the arrow Y1d. The bending portion 2b bends in connection with the operation of a bending lever 8 to be described later.

The flexible tube portion 2c has flexibility and is deformable along the nasal cavity in the state where the insertion portion 2 is inserted into the nasal cavity.

The operation portion 5 is connected to the proximal end side of the insertion portion 2. The axis in the longitudinal direction of the operation portion 5 is set substantially parallel to an insertion portion central axis 2ca which is a central axis of the insertion portion 2. In contrast, the axis in the longitudinal direction of the grasping portion 6 is set so as to substantially perpendicularly intersect with the insertion portion central axis 2*ca*.

The operation portion 5 includes a distal end surface which is perpendicular to the axis in the longitudinal direction, and the insertion portion 2 is extended from the distal end surface. The reference numeral 7A represents a break prevention member. The break prevention member 7A covers the outer circumference of the flexible tube portion 2*c* connected to the operation portion 5, to prevent buckling of the flexible tube portion 2*c*.

The operation portion 5 includes, at the proximal end portion thereof, the bending lever 8 for bending the bending portion 2*b*. The bending lever 8 includes a lever main body 8*a* and a lever fixing piece 8*b*. The end portion of the lever fixing piece 8*b* is rotatably mounted to the one side surface of the operation portion 5 with a rotational axis 8*c* which is perpendicular to the insertion portion central axis 2*ca*.

According to the configuration, the lever main body 8*a* rotates around the rotational axis 8*c* along a proximal end portion curved surface 5*r* of the operation portion 5, as shown by the arrows Y1*a* and Y1*b*. When the lever main body 8*a* is rotated around the rotational axis 8*c* in the direction shown by the arrow Y1*b*, the bending portion 2*b* is bent in the up direction, for example. Furthermore, when the lever main body 8*a* is rotated in the direction shown by the arrow Y1*a*, the bending portion 2*b* is bent in the down direction.

The grasping portion 6 is grasped by an operator, for example. The grasping portion 6 is connected to the operation portion 5 and fixed integrally thereto by screwing or adhesive bonding.

The grasping portion 6 includes a lower end surface 6*a* at a position farthest from the insertion portion central axis 2*ca*. The universal cable 4 is extended out from the lower end surface 6*a*. The reference numeral 7B represents a break prevention member. The break prevention member 7B covers the outer circumference of the universal cable 4 connected to the grasping portion 6. The break prevention member 7B prevents a signal line compliant with the image pickup section 3, for example, which is inserted through the universal cable 4, from being abruptly bent.

A protruding portion 6*c* is provided at the upper portion of an insertion-portion-side side surface 6*b* of the grasping portion 6. The protruding portion 6*c* protrudes farther toward the direction of the insertion portion 2 than the extended line, which is shown by the dashed line, of the insertion-portion-side side surface 6*b*. The protruding portion 6*c* includes an inclined surface 6*d* and a holding surface 6*e*. The holding surface 6*e* of the protruding portion 6*c* is a surface on which the middle finger, for example, of the hand grasping the grasping portion 6 of the operator is placed. The holding surface 6*e* includes a supporting portion which is substantially parallel to the insertion portion central axis 2*ca*.

Note that the reference numeral 6*g* in FIG. 1 represents a grasping portion rear surface. The grasping portion rear surface 6*g* is a surface arranged at a position substantially opposed to the insertion-portion-side side surface 6*b*.

The inclined surface 6*d* is a slope which intersects with the insertion portion central axis 2*ca* on the insertion portion side at intersecting angle θ. The intersecting angle θ of the inclined surface 6*d* is set to be an acute angle. The angle θ is set such that the distance L from the insertion portion central axis 2*ca* to the inclined surface 6*d* becomes longer as going from the intersecting point to the distal end side of the insertion portion 2.

Figure 2:
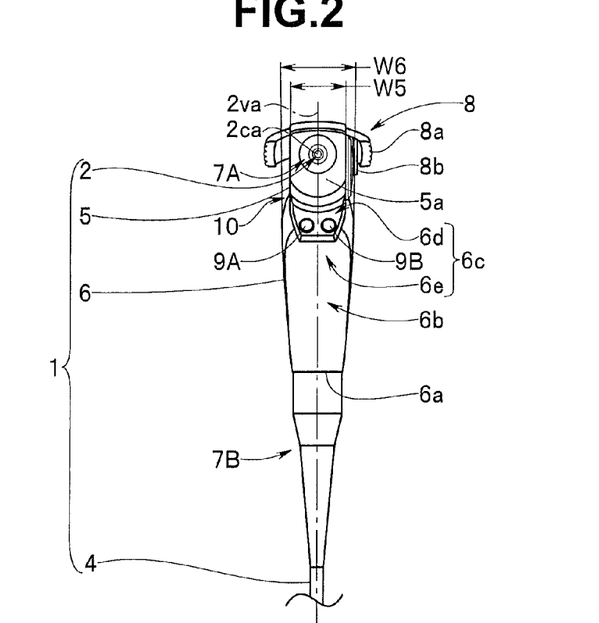
FIG. 2 is a front view of the endoscope of FIG. 1.

The inclined surface 6*d* of the protruding portion 6*c* is provided with two switch portions 9A and 9B, as shown in FIG. 2, for example. The inclined surface 6*d* has a plane on which a plurality of switch portions 9A, 9B are aligned. The switch portions 9A, 9B are push-button switches. As shown in FIG. 1, the sliding axes 9*ca* of the respective switch portions 9A, 9B are perpendicular to the plane of the inclined surface 6*d*.

The first switch portion 9A shown in FIG. 2 is assigned as a release switch for photographing an endoscopic image displayed on a display apparatus (not shown), for example. On the other hand, the second switch portion 9B is assigned as a freeze switch for temporarily stopping an endoscopic image displayed on the display apparatus, for example.

Figure 3:
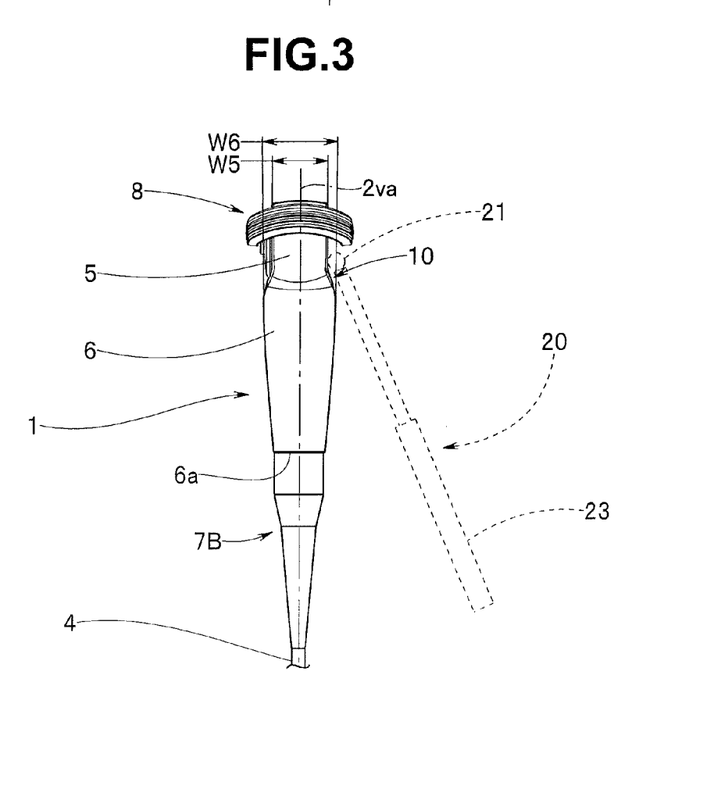
FIG. 3 is a rear view of the endoscope of FIG. 1.

As shown in FIGS. 2 and 3, the external shapes of the operation portion 5 and the grasping portion 6 are formed to be bilaterally symmetric with respect to a vertical axis 2*va* which intersects with the insertion portion central axis 2*ca*. In addition, the switch portions 9A, 9B and the lever main body 8*a* of the bending lever 8 are disposed so as to be bilaterally symmetric with respect to the vertical axis 2*va*.

Therefore, the operator can grasp the grasping portion 6 with either his/her right hand or his/her left hand. Furthermore, the operator can operate the lever main body 8*a* with the thumb of the hand grasping the grasping portion, and also can operate the first switch portion 9A and the second switch portion 9B with the index finger or the like of the hand grasping the grasping portion.

In addition, the operation portion 5 is configured to be narrower than the grasping portion 6 with respect to the direction of the axis which is perpendicular to the insertion portion central axis 2*ca* of the insertion portion 2. That is, a width dimension W5 of the operation portion 5 is set to be narrower than a width dimension W6 of the grasping portion 6 by a preset dimension. As a result, a stepped portion 10 having a preset dimension is provided on both sides of the operation portion 5.

Description will be made on the working of the endoscope 1 configured as described above.

Figure 4:
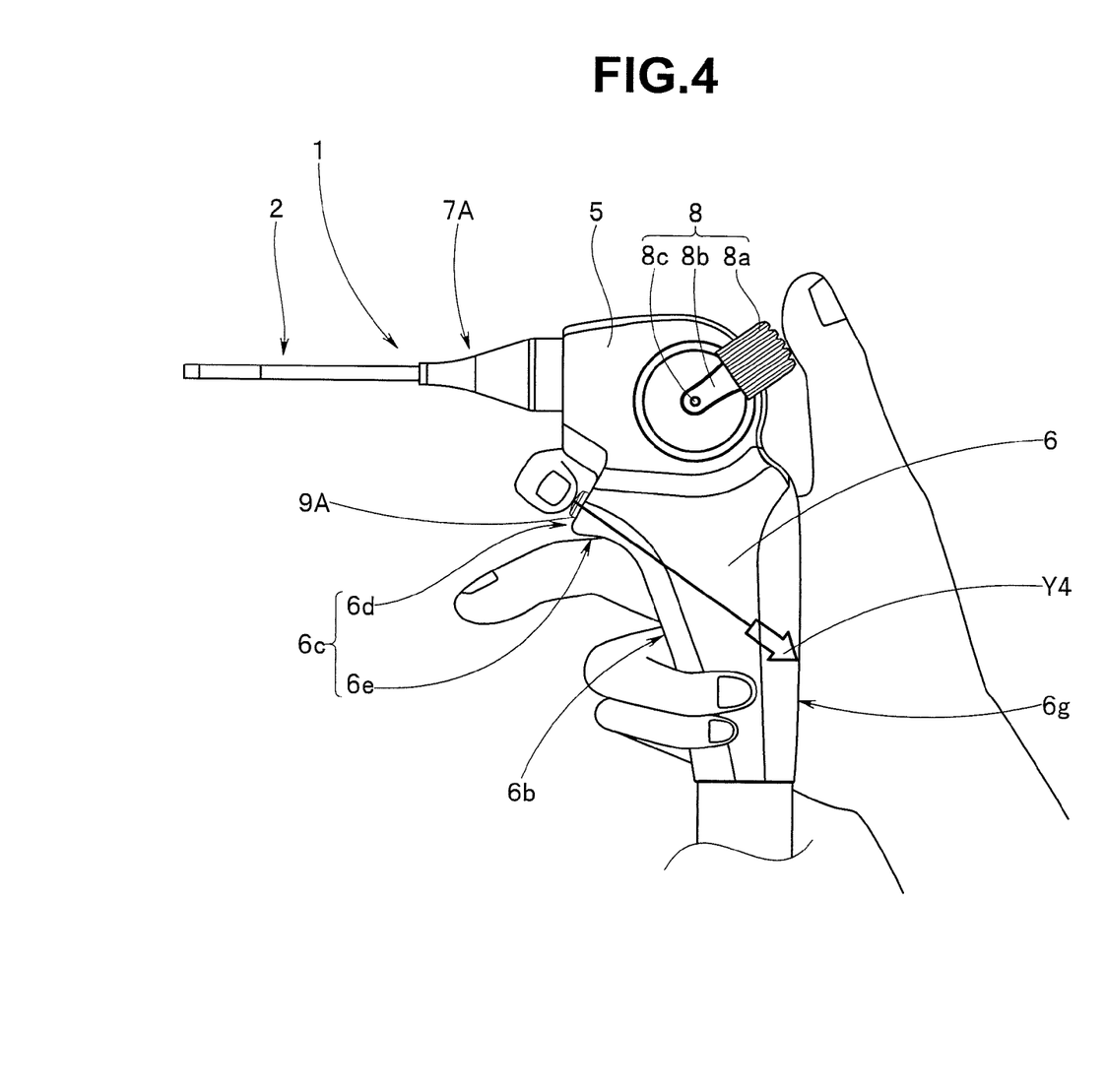
FIG. 4 is a view illustrating a grasping and operating state of the endoscope.

When operating the endoscope 1, the operator grasps the grasping portion 6 so as to wrap the grasping portion with his/her right hand, for example, as shown in FIG. 4. At this time, the operator places the thumb side of the palm of the right hand on the grasping portion rear surface 6*g* and the other parts of the palm on the right side surface of the grasping portion. Then, the operator places the thumb in the vicinity of the lever main body 8*a* and the index finger in the vicinity of the inclined surface 6*d*, to hold the insertion-portion-side side surface 6*b* with the middle, medicinal and little fingers. In this grasping state, the operator places the middle finger at the supporting portion included in the holding surface 6*e* of the protruding portion 6*c*. As a result, the operator can hold the operation portion 5 of the endoscope 1 in a stable state.

The operator grasps the operation portion 5 as described above, to insert the insertion portion 2 into the nasal cavity of the patient. At this time, the insertion-portion-side side surface 6*b* of the operation portion 5 shown in FIG. 2 is positioned in front of the eyes of the patient.

In the operation portion 5 of the endoscope 1 according to the present embodiment, the width dimension W5 of the operation portion 5 is set to be narrower than the width dimension W6 of the grasping portion 6. Therefore, when the operator inserts the distal end portion 2*a* of the insertion portion 2 from the entrance of the nasal cavity to the deep direction, the operation portion 5, the width dimension of which is narrower than the width dimension of the grasping portion 6 approaches the front of the eyes of the patient, thereby alleviating an oppressing feeling of the patient.

After inserting the insertion portion 2 into the nasal cavity, the operator appropriately operates the lever main body 8a in the arrow Y1a direction or the arrow Y1b direction to observe inside of the nasal cavity. Then, the operator photographs the diseased part and the like, as needed. At the time of the photographing, the operator performs pressing operation of the first switch portion 9A as a push-button switch.

In the endoscope 1 according to the present embodiment, the first switch portion 9A provided to the operation portion 5 is arranged on the plane of the inclined surface 6d which intersects with the insertion portion central axis 2ca at the intersecting angle θ which is an acute angle. In addition, the sliding axis of the first switch portion 9A is arranged so as to be perpendicular to the plane of the inclined surface 6d. Accordingly, the pressing direction of the first switch portion 9A pressed with the index finger of the operator, for example, is the direction of the arrow Y4 in FIG. 4 which intersects with the insertion portion central axis 2ca. Therefore, the pressing force is directed toward the palm wrapping the grasping portion rear surface 6g.

That is, the pressing force at the time of the pressing operation of the first switch portion 9A is absorbed by the hand grasping the grasping portion 6. As a result, hand jiggling which will cause the insertion portion 2 to shake in connection with the pressing operation of the first switch portion 9A is suppressed, thereby capable of easily photographing an endoscopic image with no blur.

Note that description was made above regarding the case where the first switch portion 9A is pressed. However, also in the case where the second switch portion 9B is pressed, the same working and effects can be obtained. That is, when the operator presses the second switch portion 9B in order to temporarily stop the endoscopic image displayed on the display apparatus, hand jiggling is prevented. As a result, the operator can surely display a desired endoscopic image on a display screen as a still image.

Figure 5:
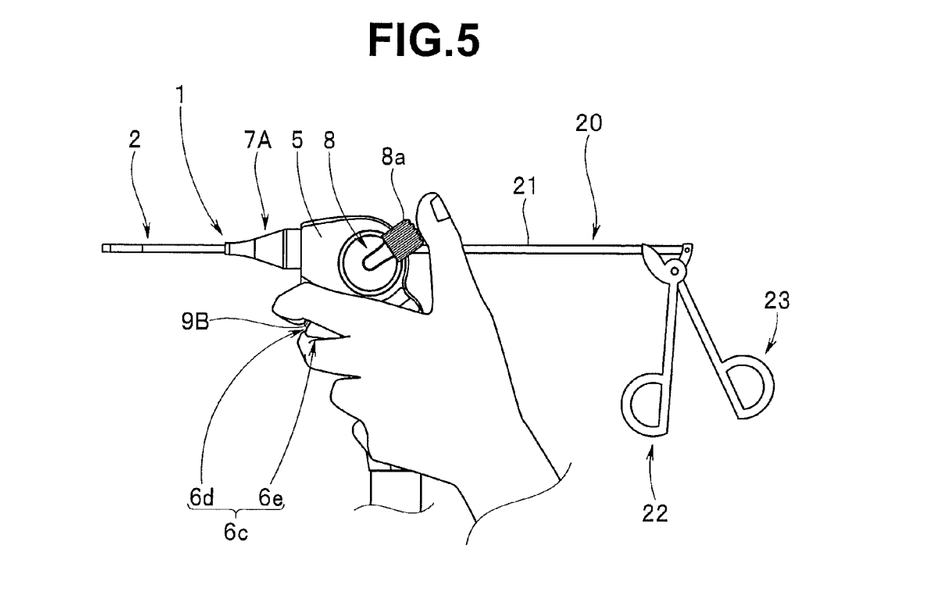
FIG. 5 is a view illustrating a relationship between the grasped endoscope and a treatment instrument.

When observing inside of the nasal cavity and finds an inflammation or a tumor, for example, the operator performs treatment by using a treatment instrument as needed. When excising a tumor, for example, the operator grasps a forceps 20, for example, which is a treatment instrument with his/her right hand while grasping the grasping portion 6 with his/her left hand, as shown in FIG. 5. Then, the operator operates the endoscope 1 with his/her left hand and excises the tumor by operating the forceps 20 with his/her right hand. Note that the reference numeral 22 represents a fixed handle, for example, and the reference numeral 23 represents a movable handle, for example.

At this time, the operator arranges a forceps inserting portion 21 of the forceps 20 at the stepped portion 10 on the right surface side of the grasping portion as shown by the dashed lines in FIG. 3.

In the operation portion 5 of the endoscope 1 according to the present embodiment, the width dimension W5 of the operation portion 5 is set to be narrower than the width dimension W6 of the grasping portion 6, and the stepped portion 10 is respectively provided on both sides of the operation portion 5. Therefore, when the operator inserts the forceps inserting portion 21 of the forceps 20 into the nasal cavity while grasping the grasping portion 6 with his/her right hand or left hand, the operation portion 5 of the endoscope 1 does not obstruct the insertion of the forceps inserting portion 21 into the nasal cavity. That is, the stepped portion 10 respectively provided on both sides of the operation portion 5 can reduce interference between the operation portion 5 of the endoscope 1 and the forceps inserting portion 21.

Note that in the above-described embodiment, the two switch portions 9A, 9B are provided on the inclined surface 6d of the operation portion 5 of the endoscope 1 so as to be symmetric across the vertical axis 2va, and a function for photographing an endoscopic image and a function for temporarily stopping the endoscopic image are assigned to the switch portions 9A and 9B, respectively. However, in recent years, in response to multifunctionality of endoscope systems, there has been a desire for further adding functional switches also regarding the switch portions provided to the operation portion. Specifically, there has been a desire for assigning a function for magnifying or reducing an endoscopic image, a function for adjusting illumination light amount, or a function for switching illumination lights, for example, to the switch portions of the operation portion, in addition to the photographing function and the temporarily stopping function.

With reference to FIGS. 6-8, and FIGS. 9-11, modified examples of the operation portion will be described.

A first modified example of the operation portion will be described with reference to FIGS. 6-8.

Figure 6:
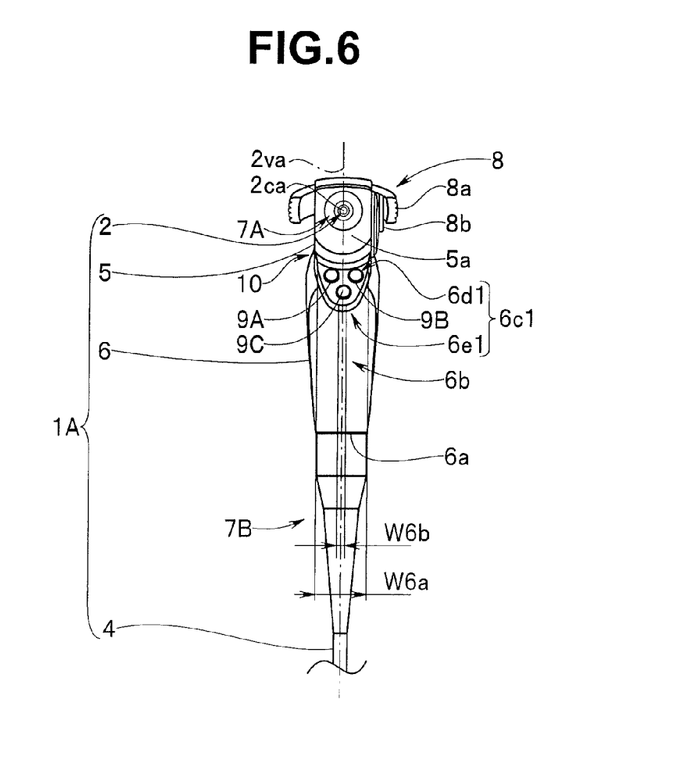
FIG. 6 relates to a first modified example of the grasping portion and is a front view describing an endoscope having three switch portions.
Figure 7:
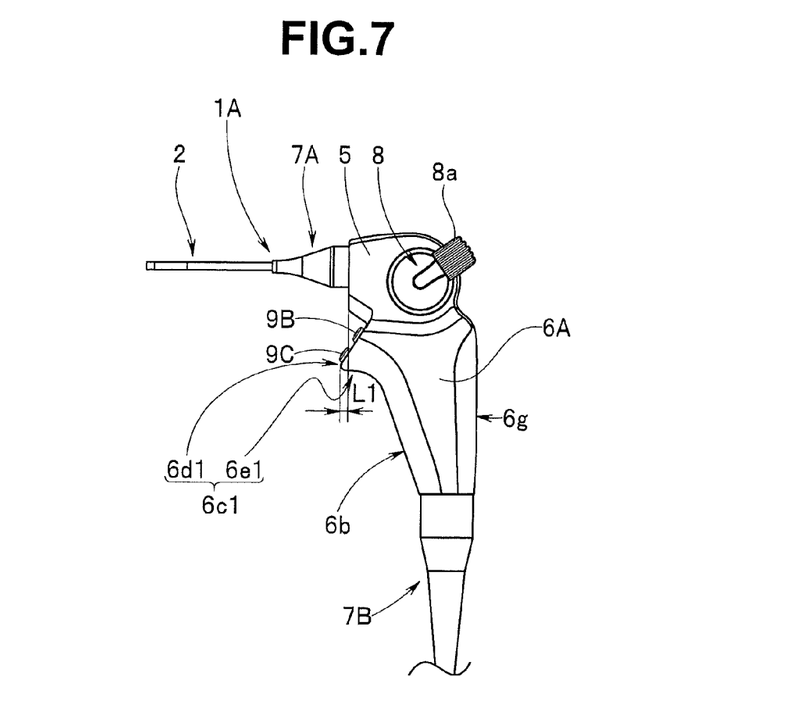
FIG. 7 is a side view of the endoscope of FIG. 6.

As shown in FIGS. 6, 7, an endoscope 1A according to the present embodiment is configured such that a protruding portion 6c1 is connected to an upper portion of an insertion-portion-side side surface 6b of a grasping portion 6A. At the protruding portion 6c1, a third switch portion 9C can be arranged in addition to the above-described two switch portions 9A and 9B.

As shown in FIG. 7, the protruding portion 6c1 protrudes farther toward the insertion portion side by a predetermined amount (L1 in the drawing) than a connecting point 5a between the insertion portion 2 and the operation portion 5. As a result, the supporting portion which is included in the holding surface 6e and substantially parallel to the insertion portion central axis 2ca is also provided so as to protrude farther than the connecting point 5a.

In addition, the protruding portion 6c1 is formed such that a distal end side width dimension W6b is smaller than a base side width dimension W6a by a preset dimension, as shown in FIG. 6. The switch portions 9A, 9B are arranged on the base side of the inclined surface 6d1, and one switch portion 9C is arranged on the distal end side. That is, the switch portions 9A, 9B and 9C are arranged such that the number of switches is reduced as going toward the direction protruding from the grasping portion 6, in other words, in the direction of the insertion portion 2.

Note that the external shapes of the operation portion 5 and the grasping portion 6A are formed to be bilaterally symmetric with respect to the vertical axis 2va. In addition, the switch portions 9A, 9B and 9C, and the lever main body 8a of the bending lever 8 are disposed so as to be bilaterally symmetric with respect to the vertical axis 2va. Furthermore, the third switch portion 9C is a push-button switch which is similar to the switch portions 9A and 9B. Also the sliding axis of the third switch portion 9C is perpendicular to the plane of the inclined surface 6d1.

According to such a configuration, when the third switch portion 9C is pressed, hand jiggling which will cause the insertion portion 2 to shake can be prevented similarly as in the above-described embodiment.

In addition, the distal end side of the protruding portion 6c1 which protrudes toward the distal end side of the insertion portion 2 is formed into a tapered shape, thereby capable of increasing a space for arranging switch portions to increase the number of the switch portions, while preventing a size increase of the operation portion 3 of the endoscope 1. In addition, when pressing the first switch portion 9A and the second switch portion 9B, it is possible to smoothly press the switch portions without being disturbed by the protruding portion 6c1.

Note that a function for switching illumination lights is assigned to the third switch portion 9C, for example. Other configurations are the same as those of the above-described endoscope 1. The same members are attached with the same reference numerals and description thereof will be omitted.

Description will be made on the working of the endoscope 1A configured as described above.

Figure 8:
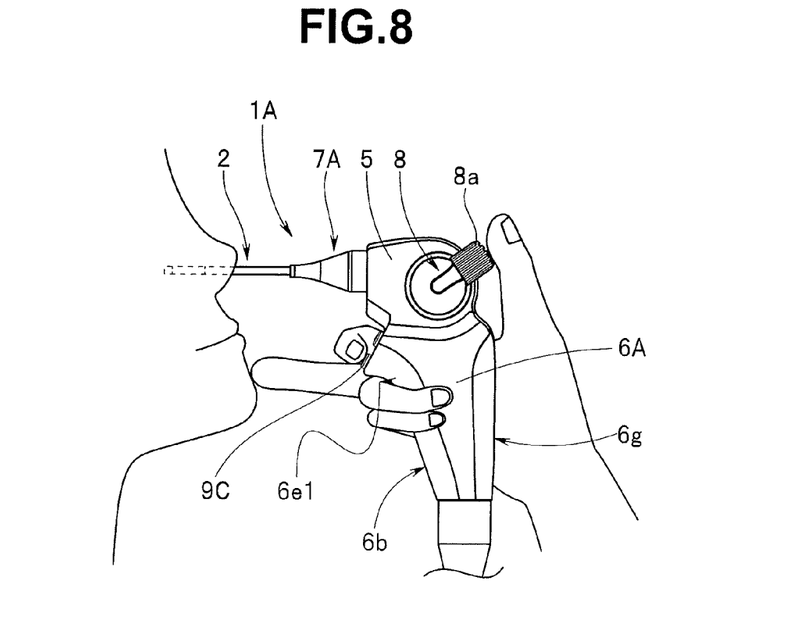
FIG. 8 is a view illustrating a grasping and operating state of the endoscope.

As shown in FIG. 8, when operating the endoscope 1A, the operator grasps the grasping portion 6A so as to wrap the grasping portion with his/her right hand, for example. At this time, the operator places the thumb side of the palm of the right hand on the grasping portion rear surface 6g and other parts of the palm on the right side surface of the grasping portion. Then, the operator may place the thumb in the vicinity of the lever main body 8a and the index finger in the vicinity of the inclined surface 6d, to hold the insertion-portion-side side surface 6b with the medicinal finger and the little finger. In the grasping state, the operator can release the middle finger from the grasping portion 6A.

Note that the operator places the middle finger at the supporting portion included in the holding surface 6e1 of the protruding portion 6c1. The finger to be released from the grasping portion 6A is not limited to the middle finger, and may be the little finger or the medicinal finger.

The operator grasps the grasping portion 6 as described above and inserts the insertion portion 2 into the nasal cavity of the patient. At that time, the operator places the middle finger released from the grasping portion 6 at the jaw of the patient, for example. At this time, the operator moves the position of the medicinal finger located at the supporting portion of the holding surface 6e1 to the distal end side of the insertion portion, for example, to ensure an optimal examination state. After that, the operator operates the lever main body 8a to bend the bending portion 2b, and observes inside of the nasal cavity.

In the present embodiment, the protruding portion 6c1 is protruded farther than the connecting point 5a by the dimension of L1, and the supporting portion included in the holding surface 6e1 is provided on the more distal end side than the connecting point 5a. As a result, the operator ensures an optimal examination state while placing the middle finger at the jaw of the patient, as described above, to be able to perform observation or medical procedure. This prevents a change of the relative position between the patient and the insertion portion 2, even if the face of the patient moves.

During observation, the operator performs operation such as photographing by pressing operation of the first switch portion 9A, temporarily stopping an endoscopic image by pressing operation of the second switch portion 9B, or switching the illumination light from the normal light to the special observation light, for example, by pressing operation of the third switch portion 9C, as needed. At this time, the pressing forces at the time of pressing operations of the switch portions 9A, 9B and 9C are directed toward the hand grasping the grasping portion 6A to be absorbed, as described above. Therefore, hand jiggling which will cause the insertion portion 2 to shake in connection with the pressing operations of the switching portions 9A, 9B, and 9C is suppressed.

As a result, it is possible to photograph an endoscopic image with no blur, stop an endoscopic image desired by the operator to display the endoscopic image on the display screen, and perform observation by switching the illumination light to a special observation light in the state where the endoscopic image desired by the operator is displayed.

In addition, in the present embodiment, the two switch portions 9A and 9B are provided at the base side of the protruding portion 6c1 formed into a tapered shape, and one switch portion 9C is provided at the distal end side of the protruding portion 6c1. In addition, the switch portions 9A, 9B and 9C are disposed so as to be bilaterally symmetric with respect to the vertical axis 2va. As a result, the switch portions 9A, 9B and 9C are prevented from being overlapped one another with respect to the direction of the vertical axis 2va. In addition, the respective switch portions 9A, 9B and 9C can be easily and surely operated with the fingers of the operator's right hand or left hand grasping the grasping portion 6A.

A second modified example will be described with reference to FIGS. 9 to 12.

Figure 9:
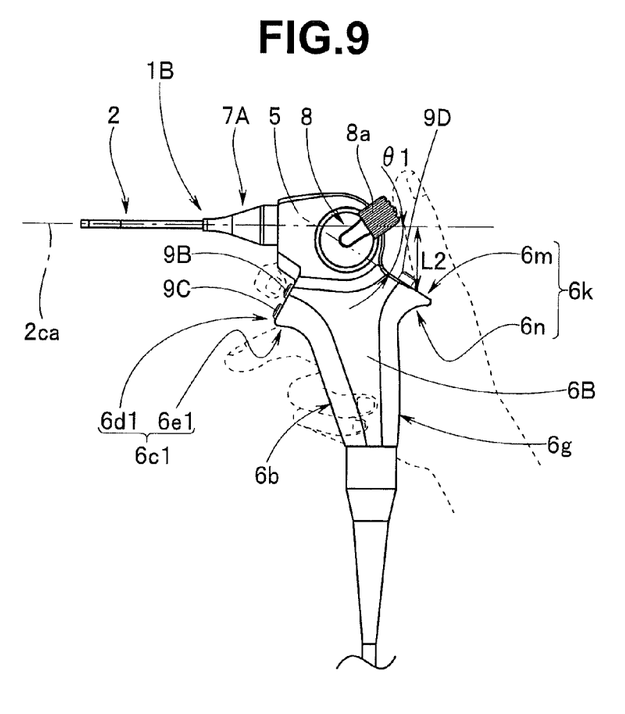
FIG. 9 relates to a second modified example of the grasping portion, and is a view illustrating an endoscope including an operation-portion-side protruding portion.
Figure 10:
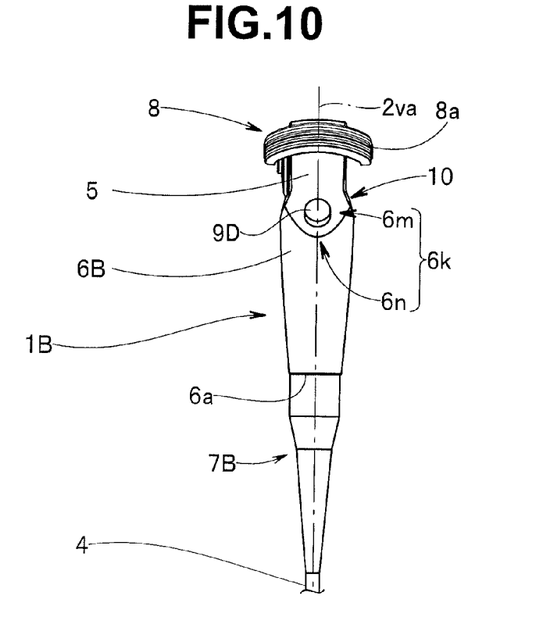
FIG. 10 is a view illustrating a grasping and operation state of the endoscope.

As shown in FIGS. 9 and 10, in an endoscope 1B according to the present embodiment, an operation-portion-side protruding portion 6k protruding farther than the extended line, shown by the dashed line, of the grasping portion rear surface 6g, is connected to the upper portion of the grasping portion rear surface 6g of the grasping portion 6B. The operation-portion-side protruding portion 6k which is further provided to the grasping portion 6B has an inclined surface 6m on which a fourth switch portion 9D can be disposed in addition to the above-described three switch portions 9A, 9B and 9C.

The operation-portion-side protruding portion 6k has the inclined surface 6m and a holding surface 6n. The holding surface 6n of the operation-portion-side protruding portion 6k is a surface on which the base part between the thumb and the index finger of the operator grasping the grasping portion 6 is placed, for example. The holding surface 6n also includes a supporting portion which is substantially parallel to the insertion portion central axis 2ca.

The inclined surface 6m is an inclined surface which intersects with the insertion portion central axis 2ca on the operation portion side at the intersecting angle θ1. The intersecting angle θ1 of the inclined surface 6m is set to be an acute angle such that the distance L2 from the insertion portion central axis 2ca to the inclined surface 6m becomes longer as getting separate from the proximal end portion of the operation portion 5 along the extended direction of the insertion portion central axis 2ca.

The inclined surface 6m has a plane on which the fourth switch portion 9D is provided, for example. The switch portion 9D is a brightness switch, for example, and has a function for gradually adjusting the brightness of an endoscopic image displayed on the display apparatus.

Note that the external shapes of the operation portion 5 and the grasping portion 6B are formed to be bilaterally symmetric with respect to the vertical axis 2va. In addition, the switch portions 9A, 9B, 9C and 9D, and the lever main body 8a of the bending lever 8 are disposed so as to be bilaterally symmetric with respect to the vertical axis 2va.

Other configurations are the same as those of the above-described endoscope 1A. The same components are attached with the same reference numerals and description thereof will be omitted.

Description will be made on the working of the endoscope 1B configured as described above.

As shown in FIG. 9, when operating the endoscope 1B, the operator grasps the grasping portion 6B so as to wrap the grasping portion with the right hand, for example, as shown by the dashed line. At this time, the operator places the thumb side of the palm of the right hand on the grasping portion rear surface 6g and other parts of the palm on the right side surface of the grasping portion. Then, the operator places the thumb in the vicinity of the lever main body 8a and the index finger in the vicinity of the inclined surface 6d, to hold the insertion-portion-side side surface 6b with the medicinal finger and the little finger.

Figure 11:
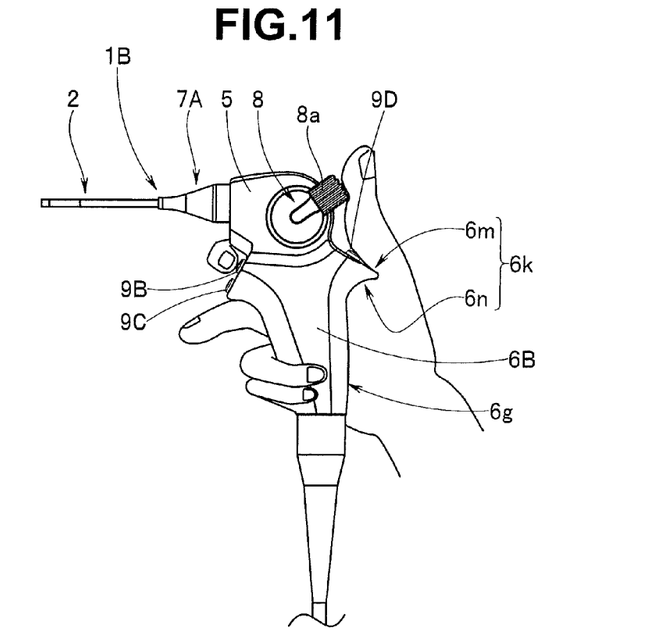
FIG. 11 a view illustrating a state where an operator operates a fourth switch without releasing his/her thumb from a bending lever.

The operator grasps the grasping portion 6B as described above and inserts the insertion portion 2 into the nasal cavity of the patient to perform observation. At this time, the operator presses the fourth switch portion 9D disposed on the inclined surface 6m, with the thumb to adjust the brightness of the endoscopic image to desired brightness. The inclined surface 6m on which the fourth switch 9D is arranged is positioned so as to form an acute angle with respect to the direction of the bending lever 8. As a result, when operating the bending lever 8 as shown in FIG. 11, the operator can operate the fourth switch 9D without releasing the thumb from the lever 8, for example.

After that, the operator appropriately operates the lever main body 8a to insert the distal end portion 2a of the insertion portion 2 to a desired position and observes inside of the nasal cavity.

Thus, in addition to the protruding portion 6c1, the operation-portion-side protruding portion 6k is provided to the grasping portion 6B. As a result, the planes of the respective protruding portions are ensured as spaces in which the switch portions are arranged.

Note that, in the present embodiment, the fourth switch portion 9D is provided on the plane of the inclined surface 6m of the operation-portion-side protruding portion 6k. However, the number of the switch portion provided on the plane of the inclined surface 6m is not limited to one, but may be plural.

Figure 12:
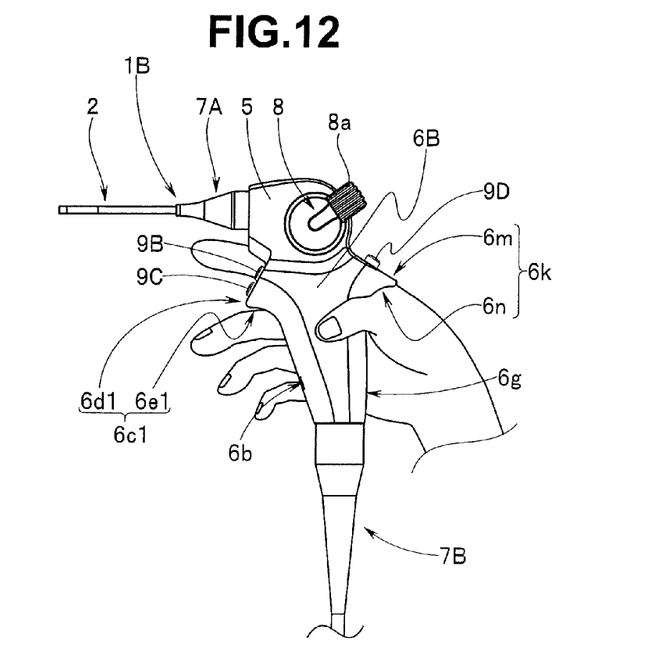
FIG. 12 is a view illustrating a state where the endoscope is held with the hand of the operator.

Note that the operation-portion-side protruding portion 6k is provided on the grasping portion rear surface 6g of the grasping portion 6 in the present embodiment. Therefore, it is possible to hold the grasping portion 6B as shown in FIG. 12. Specifically, as shown in FIG. 12, the operator places the base part between the thumb and the index finger at the supporting portion included in the operation-portion-side protruding portion 6k. On the other hand, the operator places the middle finger at the supporting portion included in the holding surface 6e1 of the protruding portion 6c1, for example. As a result, the operator can hold the operation portion 3 on the palm without grasping the grasping portion 6B with the hand. Accordingly, the operator can temporarily loosen the grasping force of the hand grasping the grasping portion 6B during the examination. This makes it possible for the operator to feel less fatigue during the examination.

Note that the present invention is not limited to the above-described embodiments but various modifications thereof are possible without departing from the gist of the invention.

What is claimed is:

1. An endoscope comprising:
an insertion portion configured to be inserted into a subject;
an image pickup section configured to pick up an image of inside of the subject;
an operation portion having an axis in a longitudinal direction set parallel to a central axis of the insertion portion, the operation portion including a distal end surface which is perpendicular to the axis in the longitudinal direction, and the insertion portion being extended from the distal end surface;
a grasping portion configured to be able to be grasped by an operator, a first end of the grasping portion being connected to the operation portion at a transition portion, the grasping portion being provided such that an axis in a longitudinal direction of the grasping portion is substantially perpendicular to the central axis of the insertion portion;
a protruding portion provided, in a protruded manner, on a surface on an insertion portion side of the grasping portion, the protruding portion extending from the first end towards a second end of the grasping portion, the protruding portion having an inclined surface which forms an acute angle with respect to the central axis of the insertion portion, on the insertion portion side; and
a switch portion provided on the inclined surface of the protruding portion and disposed at an angle which makes a right angle with respect to the acute angle, wherein
a stepped portion is formed at the transition portion such that the operation portion is configured to have a width at the transition portion which is narrower than a width of the grasping portion at the transition portion with respect to a direction of the axis perpendicular to the central axis of the insertion portion.

2. The endoscope according to claim 1, further comprising an operation-portion-side protruding portion connected to the grasping portion on a rear surface side of the insertion portion, the operation-portion-side protruding portion protruding so as to form an acute angle with respect to the central axis of the insertion portion, on the operation portion side.

3. The endoscope according to claim 1, wherein the protruding portion includes a plane on which a plurality of switches are arranged, and the switches are arranged such that the number of the switches is decreased on the plane, toward a direction protruding from the grasping portion.

4. The endoscope according to claim 1, wherein the protruding portion is configured to protrude farther toward the insertion portion side than a connecting point between the insertion portion and the operation portion.

5. The endoscope according to claim 1, wherein a function for photographing an endoscopic image, a function for temporarily stopping an endoscopic image, a function for switching an illumination light of a light source apparatus, or a function for expanding and reducing an endoscopic image is assigned to the switch portion.

6. The endoscope according to claim 1, wherein the operation portion includes a lever configured to rotate with an axis perpendicular to the central axis of the insertion portion as a rotational axis, and a bending direction of the insertion portion is controlled by the operation of the lever.

7. The endoscope according to claim 1, wherein the axis perpendicular to the central axis is a vertical axis which intersects with the central axis.

* * * * *